(12) United States Patent
Chang et al.

(10) Patent No.: US 11,266,482 B2
(45) Date of Patent: Mar. 8, 2022

(54) BALANCE MECHANISM AND MOBILE MEDICAL DEVICE HAVING THE SAME

(71) Applicant: Wistron Corporation, New Taipei (TW)

(72) Inventors: Chih-Chen Chang, New Taipei (TW); Chih-Kuan Lin, New Taipei (TW); Chi-Neng Weng, New Taipei (TW); Chih-Ying Chu, New Taipei (TW)

(73) Assignee: Wistron Corporation, New Taipei (TW)

( * ) Notice: Subject to any disclaimer, the term of this patent is extended or adjusted under 35 U.S.C. 154(b) by 323 days.

(21) Appl. No.: 16/385,773

(22) Filed: Apr. 16, 2019

(65) Prior Publication Data

US 2020/0229894 A1   Jul. 23, 2020

(30) Foreign Application Priority Data

Jan. 22, 2019   (TW) .................................. 108102441

(51) Int. Cl.
*A61B 90/50* (2016.01)
*F16M 11/42* (2006.01)
(Continued)

(52) U.S. Cl.
CPC .............. *A61B 90/50* (2016.02); *A61B 5/444* (2013.01); *A61B 6/14* (2013.01); *A61B 6/4405* (2013.01);
(Continued)

(58) Field of Classification Search
CPC ........... A61B 90/50; A61B 5/444; A61B 6/14; A61B 6/4405; A61B 2090/504;
(Continued)

(56) References Cited

U.S. PATENT DOCUMENTS 3,891,301 A * 6/1975 Heller .................... G02B 7/001
                                                    359/384
4,241,891 A * 12/1980 Rudolph .............. G10K 11/352
                                                    248/123.2
(Continued)

FOREIGN PATENT DOCUMENTS

CN          1925809 A      3/2007
CN        103256456 A      8/2013
(Continued)

OTHER PUBLICATIONS

Office Action dated May 7, 2019 in corresponding Taiwan Patent Application No. 108102441.
(Continued)

*Primary Examiner* — Christopher Garft
(74) *Attorney, Agent, or Firm* — Donald E. Stout; Stout, Uxa & Buyan, LLP (57) ABSTRACT

A balance mechanism comprises a working device, a connecting arm assembly having a variable length, a torque-balancing assembly, a weighting member, and a connecting member. The connecting arm assembly couples to the working device. The connecting arm assembly is pivoted to the torque-balancing assembly by a pivot. The weighting member couples to the torque-balancing assembly. The connecting member connects the connecting arm assembly and the torque-balancing assembly. As the distance between the working device and the pivot changes, the distance between the weighting member and the pivot changes accordingly, so that a dynamic balance can be achieved.

20 Claims, 6 Drawing Sheets

(51) Int. Cl.
　　　*F16M 11/04*　　　(2006.01)
　　　*F16M 11/08*　　　(2006.01)
　　　*A61B 5/00*　　　(2006.01)
　　　*A61B 6/00*　　　(2006.01)
　　　*A61B 6/14*　　　(2006.01)

(52) U.S. Cl.
　　　CPC ........... *F16M 11/046* (2013.01); *F16M 11/08* (2013.01); *F16M 11/42* (2013.01); *A61B 2090/504* (2016.02); *F16M 2200/028* (2013.01); *F16M 2200/041* (2013.01); *F16M 2200/066* (2013.01)

(58) Field of Classification Search
　　　CPC ...... F16M 11/046; F16M 11/08; F16M 11/42; F16M 2200/028; F16M 2200/041; F16M 2200/066; F16M 2200/06; F16M 2200/063
　　　USPC .............................. 248/325, 331, 364, 123.2
　　　See application file for complete search history.

(56) References Cited

U.S. PATENT DOCUMENTS

| | | | | |
|---|---|---|---|---|
| 5,173,802 | A * | 12/1992 | Heller | F16M 11/08 359/384 |
| 5,667,186 | A * | 9/1997 | Luber | F16M 11/08 248/550 |
| 5,712,482 | A * | 1/1998 | Gaiser | A61B 6/4405 250/363.08 |
| 6,833,950 | B2 * | 12/2004 | Schmidt | A61B 90/25 359/384 |
| 2001/0027313 | A1 * | 10/2001 | Shimmura | A61B 90/50 606/1 |
| 2004/0057718 | A1 * | 3/2004 | Chapman | F16M 11/10 396/428 |
| 2005/0167550 | A1 * | 8/2005 | Poxleitner | F16M 11/10 248/125.2 |
| 2008/0017454 | A1 * | 1/2008 | Fischer | B66B 17/12 187/264 |
| 2010/0142039 | A1 * | 6/2010 | Hammer | F16M 11/42 359/384 |
| 2011/0162476 | A1 * | 7/2011 | Nakamura | A61B 90/50 74/490.01 |
| 2012/0219121 | A1 * | 8/2012 | Simmons | A61B 6/4405 378/198 |
| 2019/0209264 | A1 * | 7/2019 | Seo | B25J 9/1065 |
| 2019/0211947 | A1 * | 7/2019 | Butcher | F16L 3/26 |

FOREIGN PATENT DOCUMENTS

| | | |
|---|---|---|
| CN | 103982759 A | 8/2014 |
| JP | 2013167878 A | 8/2013 |
| JP | 2015188565 A | 11/2015 |
| TW | 201040099 A | 11/2010 |
| TW | M433066 U | 7/2012 |
| TW | M522647 U | 6/2016 |

OTHER PUBLICATIONS

Office Action dated Mar. 31, 2021 in corresponding Chinese Patent Application No. 201910114262.3.

* cited by examiner

BALANCE MECHANISM AND MOBILE MEDICAL DEVICE HAVING THE SAME

CROSS-REFERENCE TO RELATED APPLICATIONS

The entire contents of Taiwan Patent Application No. 108102441, filed on Jan. 22 2019, from which this application claims priority, are expressly incorporated herein by reference.

BACKGROUND OF THE INVENTION

1. Field of the Invention

The present disclosure relates to a balance mechanism and a mobile medical device, such as a mobile medical trolley or cart, having the balance mechanism.

2. Description of Related Art

Apparatus or devices commonly used in daily life, especially medical devices, must be designed with their weight configuration in mind to prevent changes in weight balance during use or operation of the apparatus or device, which may result in danger to the user.

For example, Taiwan Patent Publication No. M433066, discloses a "connector capable of bridging chair leg to form device-supporting frame." The connector is suitable for connecting an office computer chair, and mainly includes a connecting base, a telescopic sliding set, a supporting mechanism, and a torque-balancing set. The connection base connects to a center leg of the computer chair. One end of the telescopic slide set connects to the left side of the connecting base, and the other end of the telescopic slide set connects to the supporting mechanism. The telescopic slide set is used to adjust the distance between the supporting mechanism and the center leg. The supporting mechanism is wheeled for in contact with the ground. The upper portion of the supporting mechanism can be connected to a notebook holder for holding a notebook computer. The torque-balancing set attaches to the right side of the connecting base and includes a weighting bar and a weighting block to balance the weight of the entire connector.

Taiwan Patent Publication No. TW201813487A discloses a supporting stand that comprises a body and a bracket. The base includes a sliding rail structure, which includes a first rail and a second rail. The bracket is slidably disposed on the sliding rail structure and adapted to slide along the first rail and the second rail. When the bracket slides along the first rail, the bracket moves upward or downward relative to the base, and when the bracket slides along the second rail, a tilting angle between the bracket and the base is changed.

Chinese Patent Application No. CN104220003A discloses an "X-ray imaging apparatus" used for X-rays detection of head and teeth. As described in the specification, the conventional X-ray imaging apparatus has a head image-capturing portion at the end of a supporting arm extending on one side of a lifter, and a panoramic image portion is mounted in front thereof. When overlooking the existing X-ray imaging apparatus, the head image-capturing portion and the panoramic image portion are both disposed at one side with the base as the center, causing a change of the barycenter of the apparatus.

In order to solve the above problems, the patent provides an X-ray imaging apparatus including an X-ray generator that generates X-rays, an X-ray detector that detects X-rays emitted from the X-ray generator, and a shutter that passes through a portion of X-rays and blocks the remaining X-rays. The X-ray imaging apparatus is characterized by further comprising a supporting mechanism that not only supports the X-ray generator and the X-ray detector but also changes the heights of the X-ray generator and the X-ray detector. The X-ray generator and the X-ray detector are disposed on the left and right sides relative to the center of the supporting mechanism for weight balance.

US Patent Publication No. US 2008/0090199 discloses a dental optical diagnostic apparatus having a main body. The inside of the main body contains various light sources and optical systems thereof, a detector and a demodulator of signal light, an optical image visualizing circuit, an image display circuit and an image processing section including a signal light scanning region specifying circuit and an operation section. The optical diagnostic apparatus also comprises a pole standing up from the operation section, a display section fitted to the pole at the height of the viewer's eyes and a multi joint arm extending transversally from the front end of the pole. The multi joint arm has a pivot at the front end thereof, to which a dental diagnostic probe is fitted. The probe by turn has a pivot at the base end and an observation window at the front end and contains in the inside the optical system of the OCT apparatus for picking up a surface image and acquiring an optical tomography. The observation window at the front end of the diagnostic probe does not shake and can be brought into contact with the dental part of the subject at a predetermined site by attitude control, using the multi joint arm and the pivot of the probe. This patent does not address the safe design of preventing dumping due to changes in the center of gravity of the apparatus during the movement.

In recent years, mobile apparatus, especially mobile medical apparatus, have continued evolve in weight configuration design because of the safety requirements during use or operation and the need to comply with national regulations.

SUMMARY OF THE INVENTION

An object of the present disclosure is to provide a balance mechanism and a mobile medical device that can overcome the problem of dumping caused by changing the center of gravity due to instantaneous pulling force or uneven road during the transportation.

According to an embodiment of the disclosure, a balancing mechanism is provided to include a working device, a connecting arm assembly, a torque-balancing group, a weighting member, and a connecting member. The connecting arm assembly has a variable length and is connected to the working device. The torque-balancing assembly and the connecting arm group are pivotally connected to a pivot. The weighting member is coupled to the torque-balancing assembly. The connecting member connects the connecting arm assembly and the torque-balancing assembly. Thereby, as the distance between the working device and the pivot varies, the distance between the weighting member and the pivot caries as well, so that a dynamic balance of the balance mechanism can be achieved.

According to another embodiment of the disclosure, a mobile medical device is provided to include a supporting mechanism, a working device, a connecting arm assembly, a torque-balancing assembly, a weighting member, and a connecting member. The connecting arm assembly has a variable length and is coupled to the working device and the supporting mechanism. The torque-balancing assembly and the connecting arm assembly are pivotally connected to a pivot. The weighting member is coupled to the torque-balancing assembly. The connecting member connects the connecting arm assembly and the torque-balancing assembly. The weight of the working device and the distance between the working device and the pivot generate a first torque. The weight of the weighting member and the distance between the weighting member and the pivot generate a second torque. The second torque changes with the first torque.

DETAILED DESCRIPTION OF THE PREFERRED EMBODIMENT

Embodiments of the disclosure are now described and illustrated in the accompanying drawings, instances of which are to be interpreted to be to scale in some implementations while in other implementations, for each instance, not. In certain aspects, use of like or the same reference designators in the drawings and description refers to the same, similar or analogous components and/or elements, while according to other implementations the same use should not. According to certain implementations, use of directional terms, such as, top, bottom, left, right, up, down, over, above, below, beneath, rear, front, clockwise, and counterclockwise, are to be construed literally, while in other implementations the same use should not. While the disclosure will be described in conjunction with these specific embodiments, it will be understood that it is not intended to limit the disclosure to these embodiments. On the contrary, it is intended to cover alternatives, modifications, and equivalents as may be included within the spirit and scope of the disclosure as defined by the appended claims. In the following description, numerous specific details are set forth in order to provide a thorough understanding of the present disclosure. The present disclosure may be practiced without some or all of these specific details. In other instances, well-known process operations and components are not described in detail in order not to unnecessarily obscure the present disclosure. While drawings are illustrated in detail, it is appreciated that the quantity of the disclosed components may be greater or less than that disclosed, except where expressly restricting the amount of the components.

Figure 1:
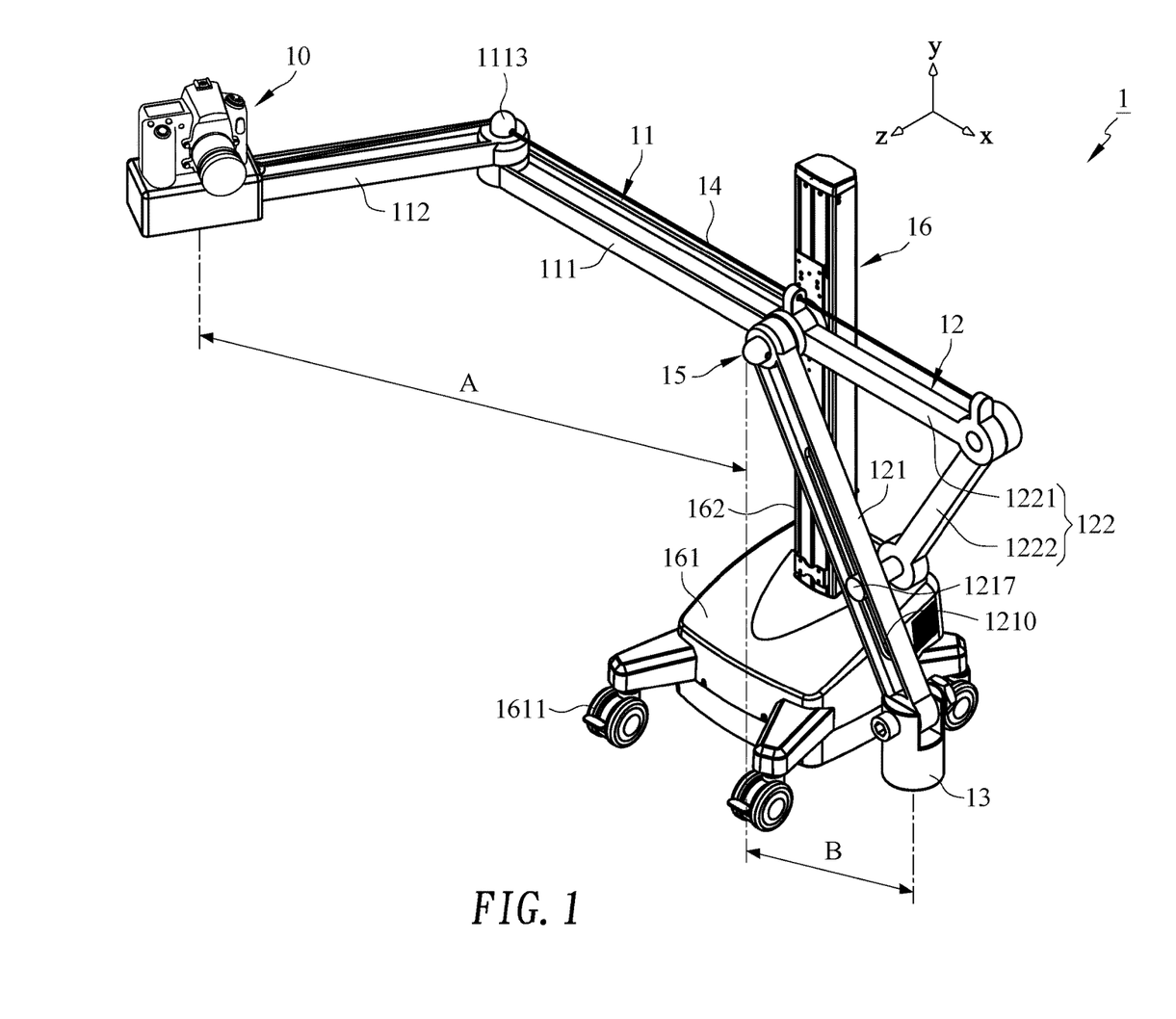
FIG. 1 is a perspective view of a balance mechanism in accordance with a preferred embodiment of the present disclosure.
Figure 2:
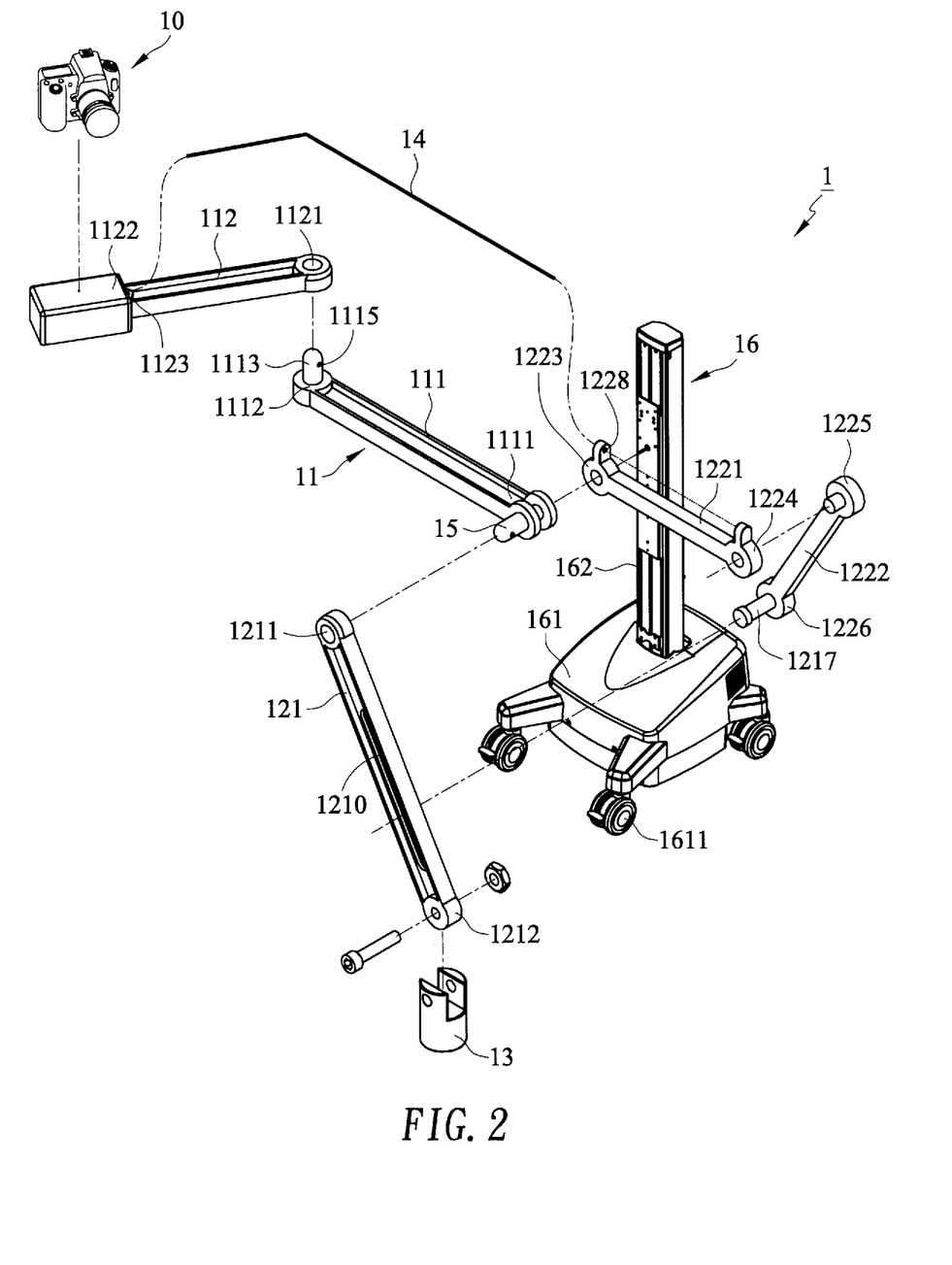
FIG. 2 is an exploded view of the balance mechanism in accordance with the preferred embodiment of the present disclosure.

FIG. 1 is a perspective view of a balance mechanism 1 in accordance with a preferred embodiment of the present disclosure. FIG. 2 is an exploded view of the balance mechanism 1 of the preferred embodiment. As shown in FIGS. 1 and 2, the balance mechanism 1 mainly includes a working device 10, a connecting arm assembly 11 having a variable length, a torque-balancing assembly 12, a weighting member 13, and a connecting member 14.

As shown in FIGS. 1 and 2, the connecting arm assembly 11 is connected to the working device 10. The torque-balancing assembly 12 and the connecting arm assembly 11 are pivotally connected to a pivot 15. The weighting member 13 is connected to the torque-balancing assembly 12. The connecting member 14 is used to connect the connecting arm assembly 11 and the torque-balancing assembly 12. In order to perform the function of the working device 10, the distance A between the working device 10 and the pivot 15 can be adjusted. When the distance between the working device 10 and the pivot 15 is changed, the distance B between the weighting member 13 and the pivot 15 is changed as well to counterbalance the weight of the working device 10, so that the center of gravity of the balance mechanism 1 will not shift significantly. In other words, a dynamic balance can be achieved for the balance mechanism 1 during the adjustment of the working device 10.

Referring to FIG. 1 and FIG. 2, in this embodiment, the connecting arm assembly 11 includes a supporting arm 111 and a movable arm 112. The first end 1111 of the supporting arm 111 and the torque-balancing assembly 12 are pivotally connected to the pivot 15, the second end 1112 of the supporting arm 111 is pivotally connected to the first end 1121 of the movable arm 112, and the second end 1122 of the movable arm 112 is connected to the working device 10. By way of illustration and without limitation, in this embodiment the pivot 15 is laterally disposed at the first end 1111 of the supporting arm 111, and the torque-balancing assembly 12 is rotatable about the pivot 15 on the xy plane. In addition, a shaft 1113 is vertically disposed at the second end of the supporting arm 111, and the movable arm 112 is rotatable about the shaft 1113 on the xz plane. Accordingly, the distance between the working device 10 and the pivot 15 can be changed by pivoting the movable arm 112 in order to perform the function of the working device 10.

Referring to FIG. 1 and FIG. 2, in this embodiment, the working device 10 can include, but is not limited to, a detecting probe, an image-capturing module, or an image-detecting module.

Referring to FIG. 1 and FIG. 2, in this embodiment, the torque-balancing assembly 12 may include, but is not limited to, a cantilever 121 and a link set 122. The first end 1211 of the cantilever 121 is pivotally connected to the pivot 15 of the connecting arm assembly 11 (for example, pivotally connected to the first end 1111 of the supporting arm 111), and the second end 1212 of the cantilever 121 is connected to the weighting member 13. The link set 122 may include, but is not limited to, a first link rod 1221 and a second link rod 1222. The first end 1223 of the first link rod 1221 is also a pivotal terminal 1223 of the link set 122 and is pivotally connected to the pivot 15. The second end 1224 of the first link rod 1221 is also a fulcrum 1224 of the link set 122 and is pivotally connected to the first end 1225 of the second link rod 1222, and the second end 1226 of the second link rod 1222 is also a slidable terminal 1226 of the link set 122 that is movably coupled with the cantilever 121. In this embodiment, the cantilever 121 has a slot 1210, and a connecting rod 1217 is laterally protruded from the second end 1226 of the second link rod 1222 (i.e., the slidable terminal 1226) of the link set 122 and is movably disposed in the slot 1210. The slidable terminal 1226 is movably coupled with the cantilever 121 by the connecting rod 1217.

It should be noted that in other embodiments of the present disclosure the link set 122 may have other configurations, which may also have the pivotal terminal 1223, slidable terminal 1226, and the fulcrum 1224, wherein the pivotal terminal 1223 and the connecting arm assembly 11 are pivotally connected to the pivot 15, the slidable terminal 1226 is movably coupled to the cantilever 121, and the fulcrum 1224 is connected to one end of the connecting member 14.

Referring to FIGS. 1 and 2, in this embodiment, the connecting member 14 may comprise, but is not limited to, a steel cable. In this embodiment, one end of the connecting member 14 is connected to a buckle 1123 disposed at the second end 1122 of the movable arm 112, and the other end of the connecting member 14 passes through a through hole 1115 of the shaft 1113 and passes through a through hole 1228 of the first link rod 1221 and then connects to the second end 1224 of the first link rod 1221.

Referring to FIGS. 1 and 2, in this embodiment, in order to perform the function of the working device 10, the distance between the working device 10 and the pivot 15 can be adjusted by pivoting the movable arm 112. In the meantime, the connecting member 14 pulls the fulcrum 1224 of the link set 122 to rotate the link set 122 about the pivot 15, and the pivoting of the link set 122 causes the cantilever 121 connected to the slidable terminal 1226 to be raised or lowered, thereby changing the distance between the weighting member 13 and the pivot 15. In this context, the distance between two objects refers to the distance measured in a horizontal straight line between the two objects.

Referring to FIGS. 1 and 2, the weight of the working device 10 multiplied by the distance between the working device 10 and the pivot 15 is a first torque, and the weight of the weighting member 13 multiplied by the distance between the weighting member 13 and the pivot 15 is a second torque. In this embodiment, when the movable arm 112 is pivoted to change the distance between the working device 10 and the pivot 15, the distance between the weighting member 13 and the pivot 15 is changed as well, and hence the first torque and the second torque are both varied. Regardless of the distance variation, the first torque is substantially equal to the second torque, or, in some embodiments, the second torque may be slightly greater than the first torque.

Referring to FIGS. 1 and 2, the balance mechanism 1 may further include a supporting mechanism 16. The supporting mechanism 16 is preferably in contact with the ground. The connecting arm assembly 11 and the torque-balancing assembly 12 are supported by the supporting mechanism 16. Preferably, the supporting mechanism 16 is movable on the ground.

As shown in FIG. 1 and FIG. 2, in this embodiment, the supporting mechanism 16 includes a movable base 161 and a post 162. In an embodiment, one end of the connecting arm assembly 11, such as the first end 1111 of the supporting arm 111, is fixed to the post 162. In another embodiment, the pivot 15 of the balance mechanism 1 is disposed on the post 162. In addition, there are several, e.g., four wheels 1611 below the movable base 161 so that the supporting mechanism 16 can be towed to move on the ground.

Figure 3:
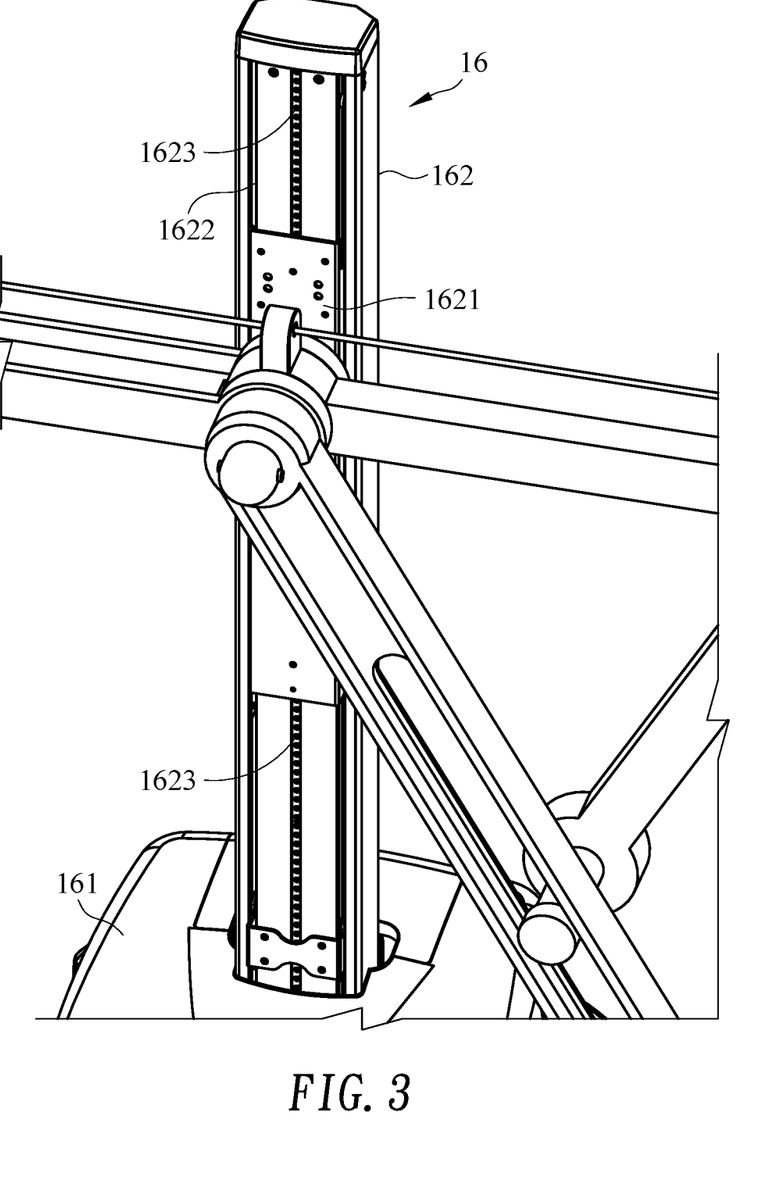
FIG. 3 is a partial perspective view of the balance mechanism provided in accordance with the preferred embodiment of the present disclosure.

FIG. 3 is a partial enlarged view of the balance mechanism 1 shown in FIG. 1. In this embodiment, the supporting mechanism 16 may further include a stepless height-adjustment structure to adjust the level of the balance mechanism 1. As shown in FIG. 3, in this embodiment, the post 162 includes a pedestal 1621 and a longitudinal track 1622. The first end 1111 of the supporting arm 111 is fixed to the pedestal 1621, which is capable of moving up and down along the longitudinal track 1622. In addition, a plurality of positioning holes 1623 are disposed along the longitudinal direction of the post 162, and a fixing member (not shown) is used for locking the pedestal 1621 to one positioning hole 1623, thereby determining a height of the connecting arm assembly 11 and the torque-balancing assembly 12.

Figure 4:
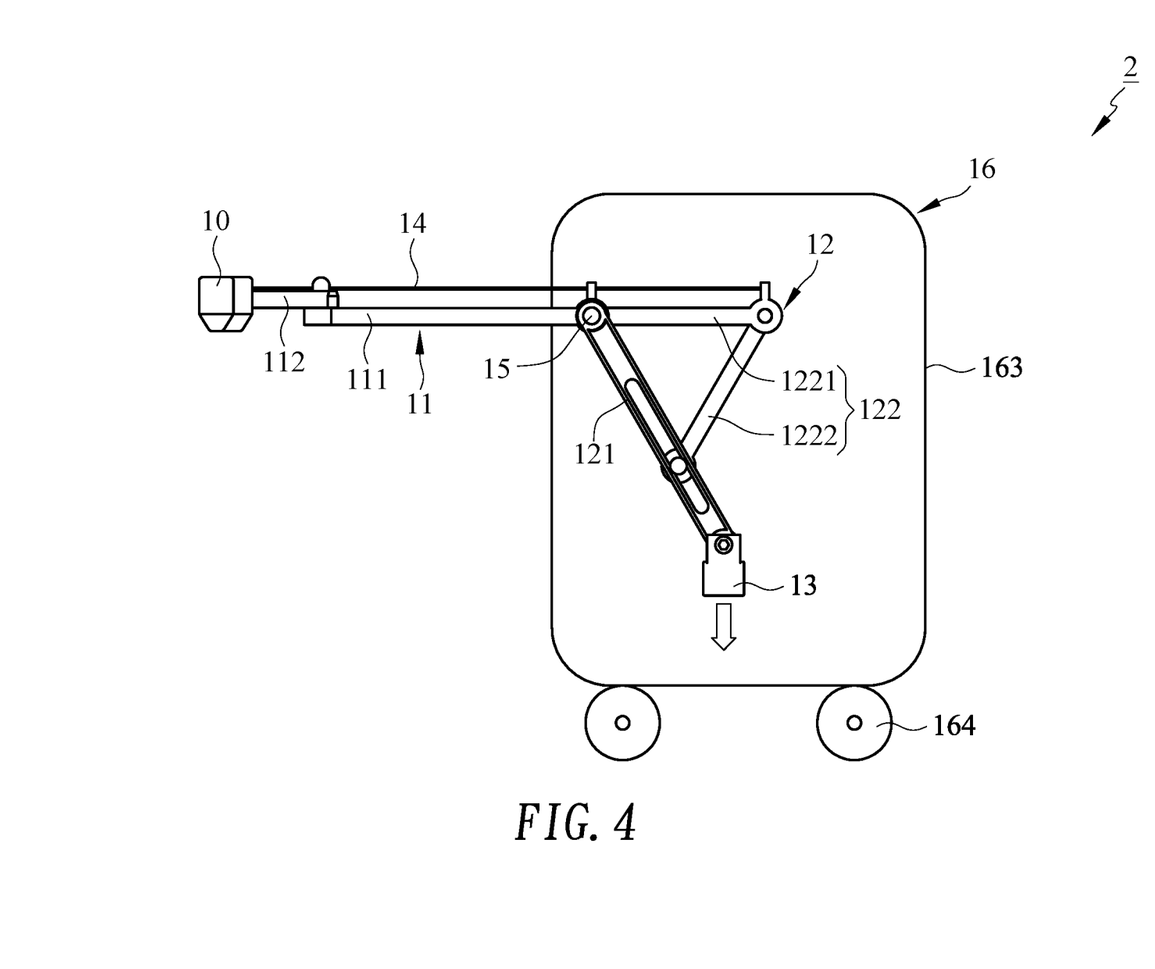
FIG. 4 is a schematic side view of a balance mechanism provided in accordance with another embodiment of the present disclosure.

FIG. 4 is a schematic side view showing a balance mechanism 2 in accordance with another embodiment of the present disclosure. In this embodiment, the balance mechanism 2 is disposed on a supporting mechanism 16. The connecting arm assembly 11 and the torque-balancing assembly 12 are supported by the supporting mechanism 16, which comprises a cart 163. One end of the connecting arm assembly 11, for example, the first end 111 of the supporting arm 111, is coupled to the cart 163. There are several, e.g., four wheels 164 below the cart 163 so that the cart 163 can be towed to move on the ground. Other details of this embodiment are the same as the embodiment described in FIGS. 1-2, and are omitted for simplicity.

Figure 5:
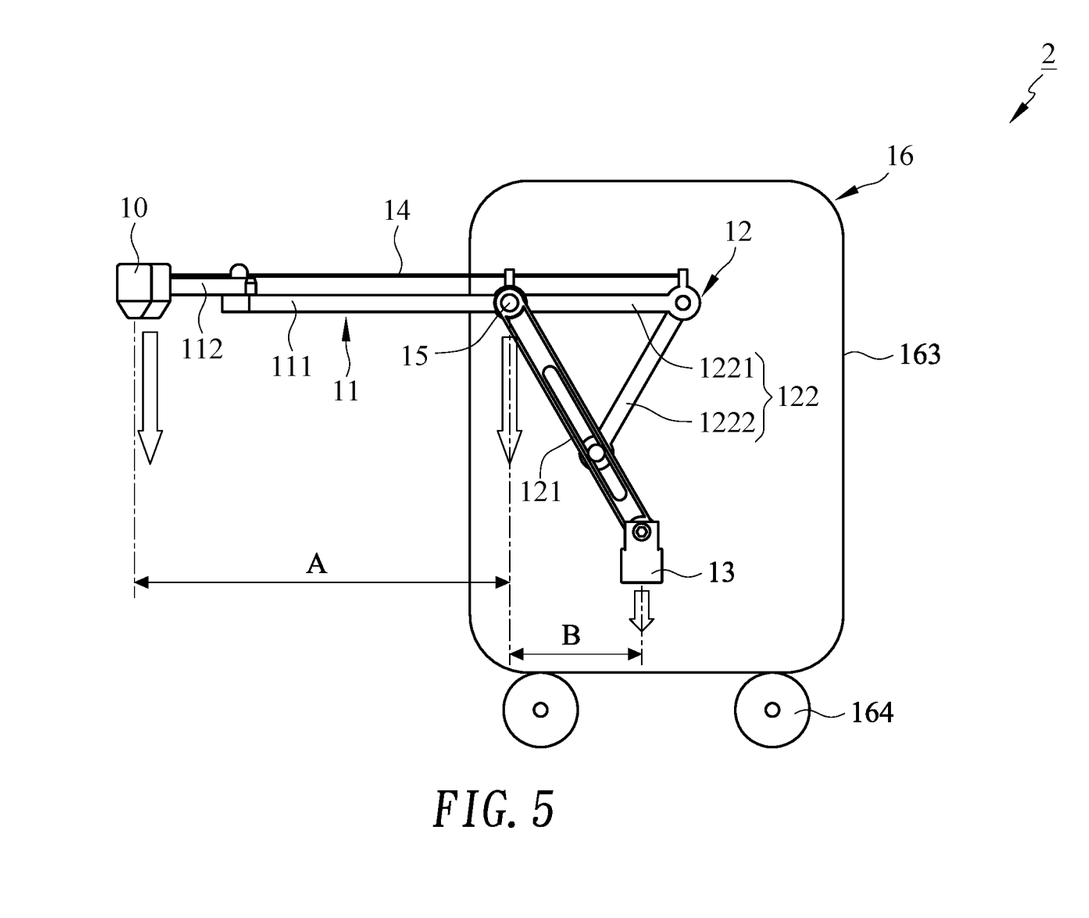
FIG. 5 is a schematic side view of the balance mechanism of FIG. 4 in accordance with the present disclosure wherein the balance mechanism is operated at a first state.
Figure 6:
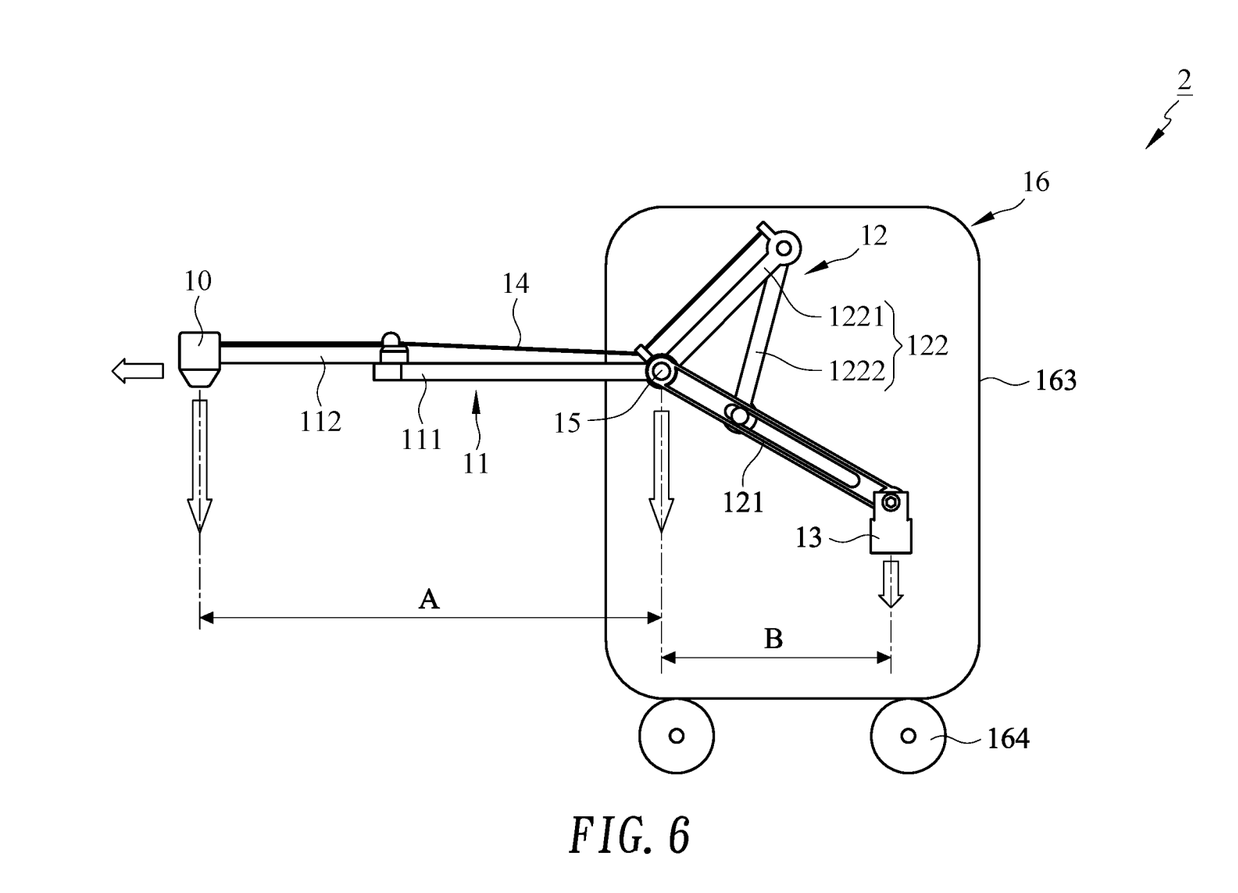
FIG. 6 is a schematic side view of the balance mechanism of FIG. 4 in accordance with the present disclosure wherein the balance mechanism is operated at a second state.

The features and advantages of the present disclosure will now be described with the balance mechanism 2 of the embodiment shown in FIG. 4. FIG. 5 is a schematic side view of the balance mechanism 2 of FIG. 4, wherein the balance mechanism 2 is operated at a first state, and FIG. 6 is a schematic side view of the balance mechanism 2 of FIG. 4, wherein the balance mechanism 2 is operated at a second state As shown in FIG. 5, in the first state, the working device 10 (e.g., a probe) of the balance mechanism 2 has a weight of 3 kg and a distance A between the working device 10 and the pivot 15 is 1 m. On the other hand, the weight of the weighting member 13 is 10 kg, and the distance B between the weighting member 13 and the pivot 15 is 0.3 m. When the balance mechanism 2 is operated at the first state, the first torque is 1×3=3 Newtons and the second torque is 0.3×10=3 Newtons (N).

As shown in FIG. 6, in the second state, when the movable arm 112 is pivoted to change the distance A between the working device 10 and the pivot 15 to 1.3 m, the first torque is changed to 1.3×3=3.9 Newtons. On the other hand, the link set 122 is pulled by the connecting member 14, so that the distance B between the weighting member 13 and the pivot 15 is changed to 0.4 m, and hence the second torque is changed to 0.4×10=4 Newtons. In the second state, the center of gravity of the balance mechanism 2 is slightly shifted to the right, and the second torque is slightly greater than the first torque, so that the entire balance mechanism 2 is not dumped during the pull of the movable arm 10.

In some embodiments of the disclosure, the balance mechanism 1 (or balance mechanism 2) is designed such that the second torque is always greater than or equal to the first torque for any operation state. Wherein, the second torque is at most 1.3 times the first torque to ensure that the balance mechanism 1 (or the balance mechanism 2) has a sufficient safety factor. In some embodiments, the weight of the weighting member 13 can be up to 1.3 times the weight of the working device 10.

The balance mechanism provided by the embodiments of the present disclosure can be applied to many devices or apparatus. In some embodiments, the balance mechanism is applied to a mobile medical device or apparatus, such as a mobile medical trolley, or a medical cart. In these applications, the working device 10 may be a medical probe, a detecting head or a camera device such as, but not limited to, a dental x-ray camera or a medical skin cancer detector.

The medical trolley and medical cart provided by the embodiments of the present disclosure can pass the relevant safety test, including the test specified in section 9.4.2.2 of IEC60601-1. The test method is as follows: the medical device is placed on a horizontal surface, and except for the patient-supporting surface any working surface of the medical device is applied with a maximum torque of 800 N, which is always downward. This working surface shall provide an apparent foothold or a surface that can sit with a minimum area of 20 cm×20 cm and a height of no more than 1 m from the ground. If the medical device overbalances, the test fails.

The medical trolley and medical cart provided by the embodiments of the present disclosure can pass the safety test specified in section 9.4.2.3 of IEC60601-1. The test method is as follows: mobile medical devices weighing more than 45 kg should be able to cross a threshold of 10 mm height without causing unacceptable risks. The medical device is configured for handling and is equipped with a secure workload at the location specified in the document. The medical device moves forward 10 times faster than normal use, spanning a solid vertical obstacle that is rectangular in cross-section, 10 mm high, 80 mm wide and fastened to the ground. Whether it's a hand-held or engine-driven mobile medical device, all wheels and casters must hit the obstacle at a speed of 0.4 m/s to 0.1 m/s, which is the maximum speed at which the device can maintain balance. It is unacceptable that medical device cannot cross this obstacle. Overbalance or any other unacceptable risk is failure.

The medical trolley and medical cart provided by the embodiments of the present disclosure can pass the safety test specified in section 9.4.2.1 of IEC60601-1. The test method is as follows: the medical device or its components cannot overbalance on a plane with a 10° inclined angle relative to the horizontal plane under any normal use of the handling state. Before testing, prepare the medical device in accordance with the requirements of the document. The medical device or its components are placed on a plane at a 10° angle relative to the horizontal. If the medical device or its components overbalance, the test fails.

The medical trolley and medical cart provided by the embodiments of the present disclosure can pass the safety test specified in section 9.4.2.2 of IEC60601-1. The test method is as follows: except for the handling state, when placed in any normal use position, the medical device or its components cannot overbalance on a 5° inclined plane relative to the horizontal.

According to the balance mechanism and the mobile medical device provided by the embodiments of the present disclosure, a dynamic balance can be achieved, and the center of gravity of the device can be prevented from being significantly changed caused by an instantaneous pulling force or tilted or uneven road during the transportation, and thereby the problem of easy to dump of the prior art can be improved.

Although specific embodiments have been illustrated and described, it will be appreciated by those skilled in the art that various modifications may be made without departing from the scope of the present disclosure, which is intended to be limited solely by the appended claims.

What is claimed is:

1. A mobile medical device, comprising:
    a supporting mechanism;
    a working device;
    a connecting arm assembly having a variable length and connecting the working device;
    a torque-balancing assembly supported by the supporting mechanism;
    a weighting member connected to the torque-balancing assembly; and
    a pivot disposed on the supporting mechanism, wherein the torque-balancing assembly and the connecting arm assembly are pivotally connected to the pivot, and one end of the connecting arm assembly is connected to the supporting mechanism;
    wherein the working device and the connecting arm assembly generate a first torque, the torque-balancing assembly and the weighting member generate a second torque, and the second torque is greater than or equal to the first torque;
    wherein a plane on which the connecting arm assembly rotates is perpendicular to a plane on which the torque-balancing assembly rotates; and
    wherein a weight of the working device multiplied by a distance between the working device and the pivot is the first torque, a weight of the weighting member multiplied by a distance between the weighting member and the pivot is the second torque, and the second torque changes with the first torque and the maximum value of the second torque is 1.3 times the first torque.

2. The mobile medical device as recited in claim 1, further comprising:
    a connecting member for connecting the connecting arm assembly and the torque-balancing assembly.

3. The mobile medical device as recited in claim 2, wherein the torque-balancing assembly comprises:
    a cantilever including a first end and a second end, the first end of the cantilever being pivotally connected to the pivot, the second end of the cantilever being connected to the weighting member; and
    a link set comprising a pivotal terminal, a slidable terminal, and a fulcrum, wherein the pivotal terminal and the connecting arm assembly are pivotally connected to the pivot, the slidable terminal is movably connected to the cantilever, and the fulcrum connects one end of the connecting member.

4. The mobile medical device as recited in claim 3, wherein the cantilever further comprises a slot, and the slidable terminal of the link set is movably coupled to the slot.

5. The mobile medical device as recited in claim 3, wherein the link set comprises:
    a first link rod comprising a first end and a second end; and
    a second link rod comprising a first end and a second end;
    wherein the first end of the first link rod is the pivotal terminal of the link set, and the second end of the first link rod is the fulcrum of the link set and is pivotally connected to the first end of the second link rod, and the second end of the second link rod is the slidable terminal of the link set.

6. A balance mechanism comprising:
    a working device;
    a connecting arm assembly having a variable length and connecting the working device;
    a torque-balancing assembly being pivotally coupled to a pivot of the connecting arm assembly; and
    a weighting member being connected to the torque-balancing assembly;
    wherein the working device and the connecting arm assembly generate a first torque, the torque-balancing assembly and the weighting member generate a second torque, and the second torque is greater than or equal to the first torque;

wherein a plane on which the connecting arm assembly rotates is perpendicular to a plane on which the torque-balancing assembly rotates; and wherein a weight of the working device and a distance between the working device and the pivot constitute the first torque, and a weight of the weighting member and a distance between the weighting member and the pivot constitute the second torque that is greater than or equal to the first torque; and a maximum value of the second torque is 1.3 times the first torque.

7. The balance mechanism as recited in claim 6, further comprising a connecting member for connecting the connecting arm assembly and the torque-balancing assembly.

8. The balance mechanism as recited in claim 7, wherein the torque-balancing assembly comprises:
a cantilever having a first end and a second end, the first end of the cantilever being pivotally connected to the pivot, the second end of the cantilever being connected to the weighting member; and
a link set having a pivotal terminal, a slidable terminal, and a fulcrum, wherein the pivotal terminal and the connecting arm assembly are pivotally connected to the pivot, the slidable terminal is movably connected to the cantilever, and the fulcrum connects to one end of the connecting member.

9. The balance mechanism as recited in claim 8, wherein the cantilever further comprises a slot, and the slidable terminal of the link set is movably disposed in the slot.

10. The balance mechanism as recited in claim 8, wherein the link set comprises:
a first link rod comprising a first end and a second end; and
a second link rod comprising a first end and a second end;
wherein the first end of the first link rod is the pivotal terminal of the link set, and the second end of the first link rod is the fulcrum of the link set and is pivotally connected to the first end of the second link rod, and the second end of the second link rod is the slidable terminal of the link set.

11. The balance mechanism as recited in claim 7, wherein the connecting member is a steel cable.

12. The balance mechanism as recited in claim 6, wherein the connecting arm assembly comprises:
a supporting arm comprising a first end and a second end; and
a movable arm comprising a first end and a second end;

wherein the first end of the supporting arm and the torque-balancing assembly are pivotally connected to the pivot, the second end of the supporting arm is pivotally connected to the first end of the movable arm, and the second end of the movable arm is connected to the working device.

13. The balance mechanism as recited in claim 6, further comprising a supporting mechanism, wherein the supporting mechanism comprises a post, and one end of the connecting arm assembly is connected to the post.

14. The balance mechanism as recited in claim 13, wherein the supporting mechanism further comprises a movable base having a plurality of wheels, and the movable base is connected to the lower end of the post.

15. The balance mechanism as recited in claim 13, wherein the post comprises a pedestal, a longitudinal track, a plurality of positioning holes, and a fixing member, and wherein one end of the connecting arm assembly is connected to the pedestal that is capable of moving up and down along the longitudinal track, and the fixing member is used for locking the pedestal to one of the plurality of positioning holes.

16. The balance mechanism as recited in claim 6, wherein the balance mechanism further comprises a supporting mechanism, which comprises a cart, and one end of the connecting arm assembly is connected to the cart.

17. The balance mechanism as recited in claim 16, wherein a plurality of wheels are disposed below the cart to enable the cart to move on the ground.

18. The balance mechanism as recited in claim 6, wherein a weight of the weighting member has a maximum value of 1.3 times a weight of the working device.

19. The balance mechanism as recited in claim 6, wherein the working device comprises a medical detecting probe or an x-ray photographing device.

20. A balance mechanism comprising:
a working device;
a connecting arm assembly having a variable length and connecting the working device;
a torque-balancing assembly being pivotally coupled to a pivot of the connecting arm assembly; and
a weighting member being connected to the torque-balancing assembly;
wherein a weight of the weighting member has a maximum value of 1.3 times a weight of the working device;
whereby when a distance between the working device and the pivot varies, a distance between the weighting member and the pivot varies as well, so that a dynamic balance of the balance mechanism is achieved.

* * * * *